(12) United States Patent
Alhaj et al.

(10) Patent No.: US 9,623,057 B1
(45) Date of Patent: Apr. 18, 2017

(54) METHOD OF MAKING A FERMENTED DAIRY PRODUCT FROM CAMEL MILK

(71) Applicant: KING SAUD UNIVERSITY, Riyadh (SA)

(72) Inventors: Omar Amin Alhaj, Riyadh (SA); Abdulrahman Saleh Al-Khalifa, Riyadh (SA); Ali Ahmed Metwalli, Riyadh (SA); Elsayed Ismail, Riyadh (SA); Hatem Salamah Ali, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/045,168

(22) Filed: Feb. 16, 2016

(51) Int. Cl.
| | | |
|---|---|---|
| *A23C 9/154* | (2006.01) | |
| *A61K 35/747* | (2015.01) | |
| *A61K 35/744* | (2015.01) | |
| *A61K 9/00* | (2006.01) | |
| *A23C 9/123* | (2006.01) | |
| *A23C 9/137* | (2006.01) | |
| *A61K 35/00* | (2006.01) | |

(52) U.S. Cl.
CPC .......... *A61K 35/747* (2013.01); *A23C 9/1238* (2013.01); *A23C 9/137* (2013.01); *A61K 9/0095* (2013.01); *A61K 35/744* (2013.01); *A23Y 2220/03* (2013.01); *A23Y 2220/15* (2013.01); *A23Y 2220/39* (2013.01); *A23Y 2240/75* (2013.01); *A61K 2035/11* (2013.01)

(58) Field of Classification Search
None
See application file for complete search history.

(56) References Cited

U.S. PATENT DOCUMENTS

| | | | |
|---|---|---|---|
| 2013/0095208 A1 | 4/2013 | Terragno et al. | |
| 2013/0251848 A1 | 9/2013 | Jacobsen et al. | |
| 2014/0037722 A1 | 2/2014 | Mousa et al. | |
| 2015/0132467 A1 | 5/2015 | Pascual et al. | |
| 2016/0100599 A1* | 4/2016 | Jacobsen | A23C 9/1216 426/43 |
| 2016/0309731 A1* | 10/2016 | Catonnet | A23C 9/137 |

FOREIGN PATENT DOCUMENTS

| | | |
|---|---|---|
| CN | 101313706 A | 12/2008 |
| CN | 101313720 A | 12/2008 |
| CN | 101176486 B | 12/2010 |
| CN | 102812993 A | 12/2012 |
| CN | 103431049 A | 12/2013 |
| RU | 2 409 963 C1 | 1/2011 |

OTHER PUBLICATIONS

Kavas N. Yoghurt Production from Camel Milk Fortified with Samphire Molasses and Different Colloids. Mljekarstvo 66(1)34-47, Jan. 2016.*
Oki K. et al. Pyrosequencing Analysis of the Microbial Diversity of Airag, Khoormog and Tarag . . . Bioscience of Microbiota, Food and Health 33(2)53-64, Jan. 1, 2013.*
Osman M. et al. Biochemical Changes Occurring During Fermentation of Camel Milk by Selected Bacterial Starter Cultures. African J of Biotechnology 9(43)7331-7336, Oct. 25, 2010.*
Hassan R. et al. Effect of Pasteurization of Raw Camel Milk and Storage Temperature on the Chemical Composition of Fermented Camel Milk. Int J of Dairy Science 2(2)166-171, 2007.*
A.H. Ibrahim et al., "The effects of various stabilizers on physicochemical properties of camel's milk yoghurt", Journal of American Science (2015), 11(1)pp. 15-24.
N.S. Al-Zoreky et al., "Suitability of Camel Milk for Making Yogurt", Food Sci. Biotechnol. (2015) 24(2), pp. 601-606.
A.B. Shori at al., "*Cinnamomum verum* improved the functional properties of bioyogurts made from camel and cow milks", Journal of the Saudi Society of Agricultural Sciences (2011) 10, pp. 101-107.
A.B. Shori et al., "Comparative antioxidant activity, proteolysis and in vitro $\alpha$-amylase and $\alpha$-glucosidase inhibition of *Allium sativum*-yogurts made from cow and camel milk", Journal of Saudi Chemical Society (2014) 18, pp. 456-463.
E.A. Eissa et al., "Physicochemical, Microbiological and Sensory Characteristics of Yoghurt Produced From Camel Milk During Storage", Electronic Journal of Environmental, Agricultural and Food Chemistry, (2011), 10(6), pp. 2305-2313.
H.G.A. Ahmadoon, "Quality Changes in Yoghurt Made From Camel Milk and Mixed Camel Milk with Cow Milk During Preservation", Red Sea University Journal (2012) 2, pp. 27-37.

* cited by examiner

*Primary Examiner* — Ralph Gitomer
(74) *Attorney, Agent, or Firm* — Richard C. Litman

(57) ABSTRACT

The method of making a fermented dairy product from camel milk includes heating camel milk at 85° C. for thirty minutes, cooling the milk to about 60° C. and adding a stabilizer or hydrocolloid (preferably 0.02% by weight κ-carrageenan) to avoid whey off (whey separation) problems, then cooling the milk and adding a probiotic bacterial culture. The camel milk is fermented at between 40° C. and 45° C. for a time ranging between 4 and 12 hours, depending upon the particular bacterial culture used. The fermented camel milk is subjected to three successive storage steps to enrich the D-amino acid, antioxidant and antimicrobial content, storing the fermented camel milk at a temperature of 10° C. for 14 hours, then storing the fermented camel milk in a cold room at a temperature of 4° C., and then storing the fermented camel milk in a refrigerator at a temperature of 4° C. for between 1 and 15 days.

3 Claims, 13 Drawing Sheets

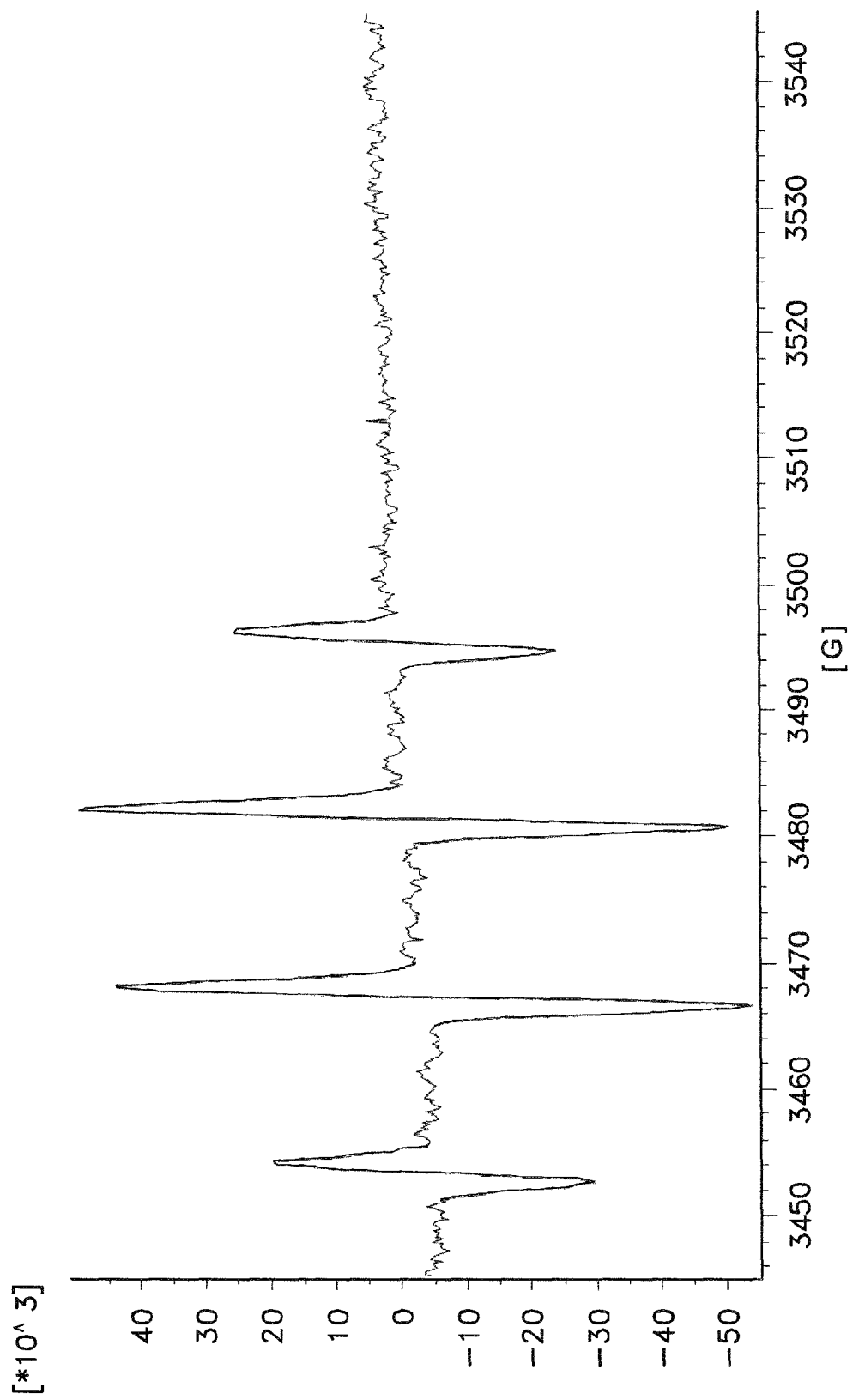

METHOD OF MAKING A FERMENTED DAIRY PRODUCT FROM CAMEL MILK

BACKGROUND OF THE INVENTION

1. Field of the Invention

The present invention relates to methods of making edible dairy products, and particularly to a method of making a fermented dairy product from camel milk.

2. Description of the Related Art

Camel milk provides an alternative to bovine milk in arid areas of the world where camels are indigenous and the high overhead costs associated with bovine dairy farms and importing, transporting, and storing bovine milk make camel milk a viable option. Camel milk is high in protein, and is reputed to be high in immunoglobulins, vitamin C and other antioxidants, and antimicrobials. It does, however, have different properties from bovine milk due to the different composition of the proteins, notably casein and whey. In today's health conscious world, bovine dairy products enriched with probiotics (such as yogurt) and probiotic drinks are commonly available commercially. However, fermented camel milk products enriched with probiotics are not so widely available due, in part, to their poor thermal stability. It would be desirable to produce a fermented dairy product from camel milk enriched with probiotics and enhanced immune system, antioxidant, and antimicrobial properties. Thus, a method of making a fermented dairy product from camel milk solving the aforementioned problems is desired.

SUMMARY OF THE INVENTION

The method of making a fermented dairy product from camel milk includes heating camel milk at 85° C. for thirty minutes, cooling the milk to about 60° C. and adding a stabilizer or hydrocolloid (preferably 0.02% by weight κ-carrageenan) to avoid whey off (whey separation) problems, then cooling the milk and adding a probiotic bacterial culture. The camel milk is then fermented at between 40° C. and 45° C. for a time ranging between 4 and 12 hours, depending upon the particular bacterial culture used. The fermented camel milk is subjected to three successive storage steps to enrich the D-amino acid, antioxidant and antimicrobial content, particularly first storing the fermented camel milk at a temperature of 10° C. for 14 hours, then storing the fermented camel milk in a cold room at a temperature of 4° C., and then further storing the fermented camel milk in a refrigerator at a temperature of 4° C. for between 1 and 15 days.

These and other features of the present invention will become readily apparent upon further review of the following specification.

BRIEF DESCRIPTION OF THE DRAWINGS

FIG. 3F is an electron paramagnetic resonance (EPR) signal (1:2:2:1) plot for DMPO-OH adduct of product P5.

Similar reference characters denote corresponding features consistently throughout the attached drawings.

DETAILED DESCRIPTION OF THE PREFERRED EMBODIMENTS

Figure 1:
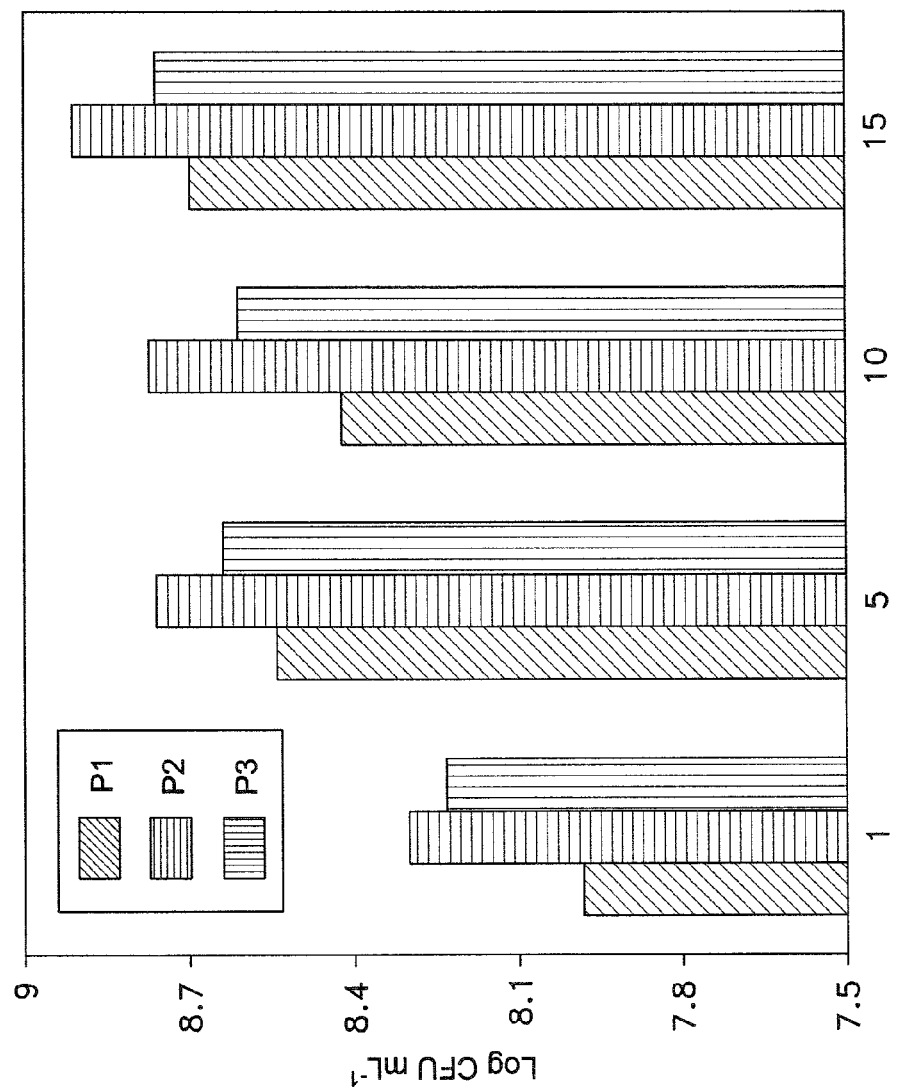
FIG. 1 is a histogram chart showing total bacterial counts as a function of storage time for fermented dairy products made from camel milk according to the present method for three mixtures of probiotic bacteria.

The method of making a fermented dairy product from camel milk produces a camel milk product enhanced by probiotics. The method of making a fermented dairy product from camel milk includes heating camel milk at 85° C. for thirty minutes, cooling the milk to about 60° C. and adding a stabilizer or hydrocolloid (preferably 0.02% by weight κ-carrageenan) to avoid whey off (whey separation) problems, then cooling the milk and adding a probiotic bacterial culture. The camel milk is then fermented at between 40° C. and 45° C. for a time ranging between 4 and 12 hours, depending upon the particular bacterial culture used. The fermented camel milk is subjected to three successive storage steps to enrich the D-amino acid, antioxidant and antimicrobial content, particularly first storing the fermented camel milk at a temperature of 10° C. for 14 hours, then storing the fermented camel milk in a cold room at a temperature of 4° C., and then further storing the fermented camel milk in a refrigerator at a temperature of 4° C. for between 1 and 15 days.

The following example illustrates the method. Fermented camel milk drink products were prepared from 15 liters of whole camel milk (3.1% fat, 8.1% SNF) collected from a private farm located in a central region of Saudi Arabia. Milk of different breeds belonging to *Camelus dromedaries* (i.e., a one-humped camel), which has a significantly different amino acid profile than bovine milk, was mixed in equal volumes and then homogenized. The camel milk was first heat treated at a temperature of 85° C. for 30 minutes to prevent protein precipitation. Following heat treatment, the camel milk is cooled to a temperature of 60° C. and a stabilizer or hydrocolloid, κ-carrageenan, was added to the camel milk at a concentration of 0.02 wt % to avoid whey off (whey separation) problems (e.g., syneresis) typically associated with camel milk fermentation.

The camel milk was then cooled and inoculated with 3% of one of three probiotic bacterial cultures. The three bacterial cultures used were a mixture of *Lactobacillus acidophilus* (1.5%) and *Streptococcus thermophilus* (1.5%) (the resultant fermented product hereinafter being referred to as product P1); a mixture of *Lactobacillus helveticus* (1.5%) and *Streptococcus thermophilus* (1.5%) (the resultant fermented product hereinafter being referred to as product P3); or a mixture of *Lactobacillus bulgaricus* (1.5%) and *Streptococcus thermophilus* (1.5%) (the resultant fermented product hereinafter being referred to as product P2). For products P1 and P2, fermentation occurred by incubation at a temperature of 40° C. for 10-12 hours (12 hours for P1 and 10 hours for P2). For product P3, fermentation occurred by incubation at a temperature of 43° C. for 4 hours. In each case, fermentation continued until the product attained a pH of 4.4 and an acidity between 0.70-0.80%.

The products were subjected three successive storage steps, in a refrigerator staring at 10° C. for 14 hours to enrich the D-amino acid, antioxidant, and antimicrobial content and properties, stored in a cold room at 4° C., and finally stored in a refrigerator for up to 15 days at 4° C. to increase the population of the cultures. For each of products P1, P2 and P3, the fermentation produced D-amino acids, antioxidants and antimicrobial compounds in the fermented product, as shown below in Tables 1, 2, 3 and 4.

Table 1 below shows the D-amino concentrations for products P1, P2 and P3, as described above, as well as control products of unfermented camel milk supplemented with carrageenan (product P4), and unfermented camel milk without carrageenan (product P5). In Table 1, Asx=Asn+Asp; and Glx=Gln+Glu, where Asn and Gln are amides (hydrolyzed to aspartic and glutamic acid). Amino acids were isolated by solid-phase extraction (SPE). The results in Table 1 are shown for products produced with one day of storage at 4° C.

The D-AA content in products P1, P2 and P3 were detected to determine the differences in the fermented camel milk products due to the presence of various added strains. The D-AA content in products P4 and P5 were detected to determine if carrageenan in unfermented camel milk products has additional health effects during its presence in camel milk. Protein concentrate recovery of D- and L-amino acid samples were derivatized and then detected, and standards were injected and identified. The isolation of amino acids and the derivatization procedures were based on SPE, thus saving time on prior removal of proteins and interfering substances.

Typically, SPE is performed using a proprietary cation-exchange mechanism. The acid solution of the internal standard ensures that the free amino acids are in an anionic form suitable for cationic binding. The alkaline nature of the elution medium ensures that the amino acid (AA) cations are released prior to derivatization. The latter involves production of chloroformate derivatives of both the amino and carboxylic acid groups.

Portions of 150 g of the fermented camel milk were homogenized with a magnetic stirrer and centrifuged at 1,600 g for 15 minutes. The precipitate was discarded, and the supernatant was adjusted to a pH of 2.0 by addition of trifluoroacetic acid (TFA). The solution was passed through a cation exchanger (200-400 mesh). After washing with water (20 mL), the samples were eluted with 2M aqueous ammonia. The eluate was evaporated to dryness in vacuum, and the residue was dissolved in 10 mL of 0.1% aqueous TFA. The solution was subjected to successive ultrafiltrations using a micro-volume stirred ultrafiltration cell using 25 mm membranes with cut-off sizes of 10, 5 and 1 kDa. The eluate of the 1 kDa fraction was evaporated to dryness in vacuum and dissolved in 1 mL of 0.1% TFA. Aliquots of 20 mL were used for gas chromatography-mass spectrometry (GC-MS).

In Table 1, relative amounts of D-AAs are calculated as % D-AA=$100 \times A_D/(A_D+A_L)$, where % D-AA is the relative amount of the D-enantiomer, and $A_D$ and $A_L$ are the peak areas of the D- or L-enantiomer, respectively.

TABLE 1

D-amino acid concentrations (% D-AA) in products P1, P2, P3, P4 and P5

| D-Amino Acid | P1 (% D-AA) | P2 (% D-AA) | P3 (% D-AA) | P4 (% D-AA) | P5 (% D-AA) |
|---|---|---|---|---|---|
| Ala | 10.98 | 8.15 | 13.69 | 2.12 | 2.09 |
| Val | 11.26 | 10.40 | 10.15 | 7.11 | 8.60 |
| Thr | 0.34 | 0.65 | 0.26 | 0.516 | 0.15 |
| allo Thr | 0.74 | 0.22 | 1.25 | 0.38 | 0.93 |
| IsoLeu | 5.89 | 5.55 | 4.44 | 3.96 | 3.77 |
| Pro | 0.50 | 0.21 | 0.14 | 0.21 | 0.17 |
| Leu | 3.60 | 4.48 | 3.86 | 3.58 | 3.50 |
| Ser | 0.25 | — | 0.22 | 0.16 | 0.04 |
| Cys | n.d | n.d | n.d | n.d | n.d |
| Asp | 5.94 | 2.47 | 3.27 | 3.15 | 3.08 |
| Asx | — | — | — | — | — |
| Met | 6.12 | 0.95 | 2.72 | 4.43 | 2.99 |
| Phe | 4.54 | 4.15 | 6.19 | 3.54 | 5.39 |
| Glu | 3.13 | 2.07 | 2.88 | 1.47 | 1.02 |
| Glx | — | — | — | — | — |
| Tyr | 3.18 | 2.51 | 3.52 | 3.10 | 3.14 |
| Orn | 10.42 | 10.53 | 13.64 | 15.56 | 11.29 |
| Lys | 8.91 | 6.18 | 3.38 | 6.04 | 6.58 |
| Arg | 25.51 | 26.71 | 9.64 | 18.08 | 15.09 |
| Trp | n.d | n.d | n.d | n.d | n.d |

In general, most of the D-AA contents in products P4 and P5 were similar, except for a small increase in D-Orn and D-Arg in product P4. However, the addition of various strains to camel milk has enhanced the D-AA content, resulting in further production of D-amino acids. It was found that D-Ala, D-Val, D-Orn, D-Lys and D-Arg are the most abundant D-AAs in fermented camel milk products (P1, P2 and P3). On the other hand, lower contents of D-AAs were also detected, including D-IsoLeu, D-Asp, D-Met, D-Phe, D-Glu and D-Tyr, as shown above in Table 1. The percentage (1.48%) of D-aspartic acid in untreated raw milk was also found to increase in dairy products due to increases of treatments involved in the product's processing, including *acidophilus* milk (2.05%); kefir (2.44%); and yogurt (3.12%). These percentages are close to those detected in products P1 and P3.

The occurrence of D-AAs in unfermented camel milk products (P4 and P5) originates from digestion and autolysis of contaminant bacteria cell wall proteins (peptidoglucan) as well as milk processing and storage. In comparison to unfermented products, the increase of D-Ala, D-Val and D-Glu in fermented camel milk products (P1, P2 and P3) is attributed to the increase of total bacterial counts (i.e., an increase in cell wall proteins digestion) in fermented milk products during storage. Thus, D-Ala content (along with microbial count and ammonia content) has been recommended to be used as indicators for milk contamination.

Table 2 below shows 2,2-diphenyl-1-picrylhydrazyl (DPPH) radical scavenging assay results for products P1, P2, P3, P4 and P5, as described above. Table 3 shows similar results for hydroxyl radical scavenging activity for each product. As with the results of Table 1, the results are shown for products stored for one day at 4° C. Values within a row having different superscripts are significantly different (p≤0.05); where letters indicate significant differences among treatments by one-way ANOVA followed by Duncan's multiple range test (a>b>c).

TABLE 2

DPPH radical scavenging assay of products P1, P2, P3, P4 and P5

| Camel milk products | DPPH radical scavenging (%) | DPPH radical scavenging (μmol Trolox equivalents/ mg of protein) |
|---|---|---|
| P1 | 9.9 ± 0.8$^a$ | 0.08 ± 0.0$^a$ |
| P2 | 5.3 ± 1.7$^b$ | 0.06 ± 0.0$^b$ |
| P3 | 1.0 ± 0.8$^c$ | 0.03 ± 0.0$^c$ |
| P4 | 2.1 ± 0.1$^c$ | 0.04 ± 0.0$^c$ |
| P5 | 1.7 ± 0.7$^c$ | 0.04 ± 0.0$^c$ |

TABLE 3

Hydroxyl radical scavenging activity of products P1, P2, P3, P4 and P5

| Camel milk products | Hydroxyl radical scavenging (%) | Hydroxyl radical scavenging (μmol histidine equivalents/mg of protein) |
|---|---|---|
| P1 | 40.5 ± 0.5$^a$ | 7.4 ± 0.1$^a$ |
| P2 | 36.4 ± 0.1$^b$ | 6.4 ± 0.0$^b$ |
| P3 | 25.6 ± 1.4$^d$ | 3.7 ± 0.3$^d$ |
| P4 | 36.1 ± 0.3$^b$ | 6.3 ± 0.1$^b$ |
| P5 | 30.3 ± 1.7$^c$ | 4.9 ± 0.4$^c$ |

The 2,2-diphenyl-1-picrylhydrazyl (DPPH) radical scavenging activity of products P1, P2, P3, P4 and P5 was determined from samples (1.0 mg/mL, 250 μL) in distilled water, which were added to 1 mL of methanolic solution of DPPH (0.30 mM), vortexed, and allowed to stand at room temperature in the dark. One milliliter of the mixture was passed to the sample cavity of an electron paramagnetic resonance (EPR) spectrometer, and the spectrum was recorded. A standard curve was developed using trolox (50-500 μM in methanol). The parameters of the EPR spectrometer were set as follows: 5.02×102 receiver gain, 1.86 G modulation amplitude, 2.621 sec sweep time, 8 scans, 100.00 G sweep width, 3495.53 G center field, 5.12 ms time constant, 9.795 GHz microwave frequency, 86.00 kHz modulation frequency, and 1.86 G modulation amplitude. DPPH radical scavenging capacities were calculated as: DPPH radical scavenging capacity (%)=[(EPR signal intensity for the control−EPR signal intensity for the sample)/EPR signal intensity for the control]×100. The DPPH radical scavenging activity as shown in Table 2 above was expressed as micromoles of trolox equivalents per milligram of protein.

Figure 2A:
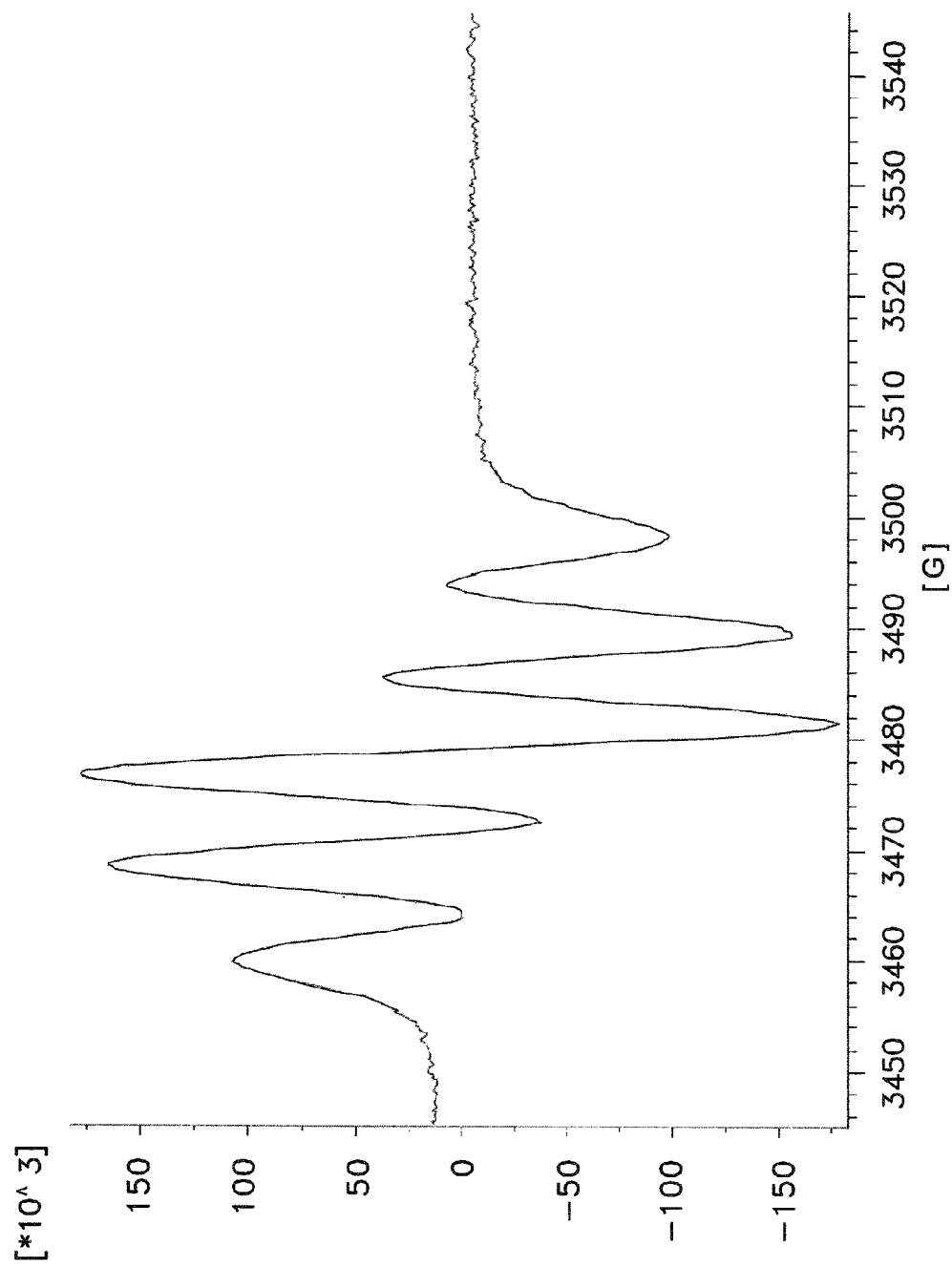
FIG. 2A is an electron paramagnetic resonance (EPR) signal plot for 2,2-diphenyl-1-picrylhydrazyl (DPPH) scavenging of a control sample.
Figure 2B:
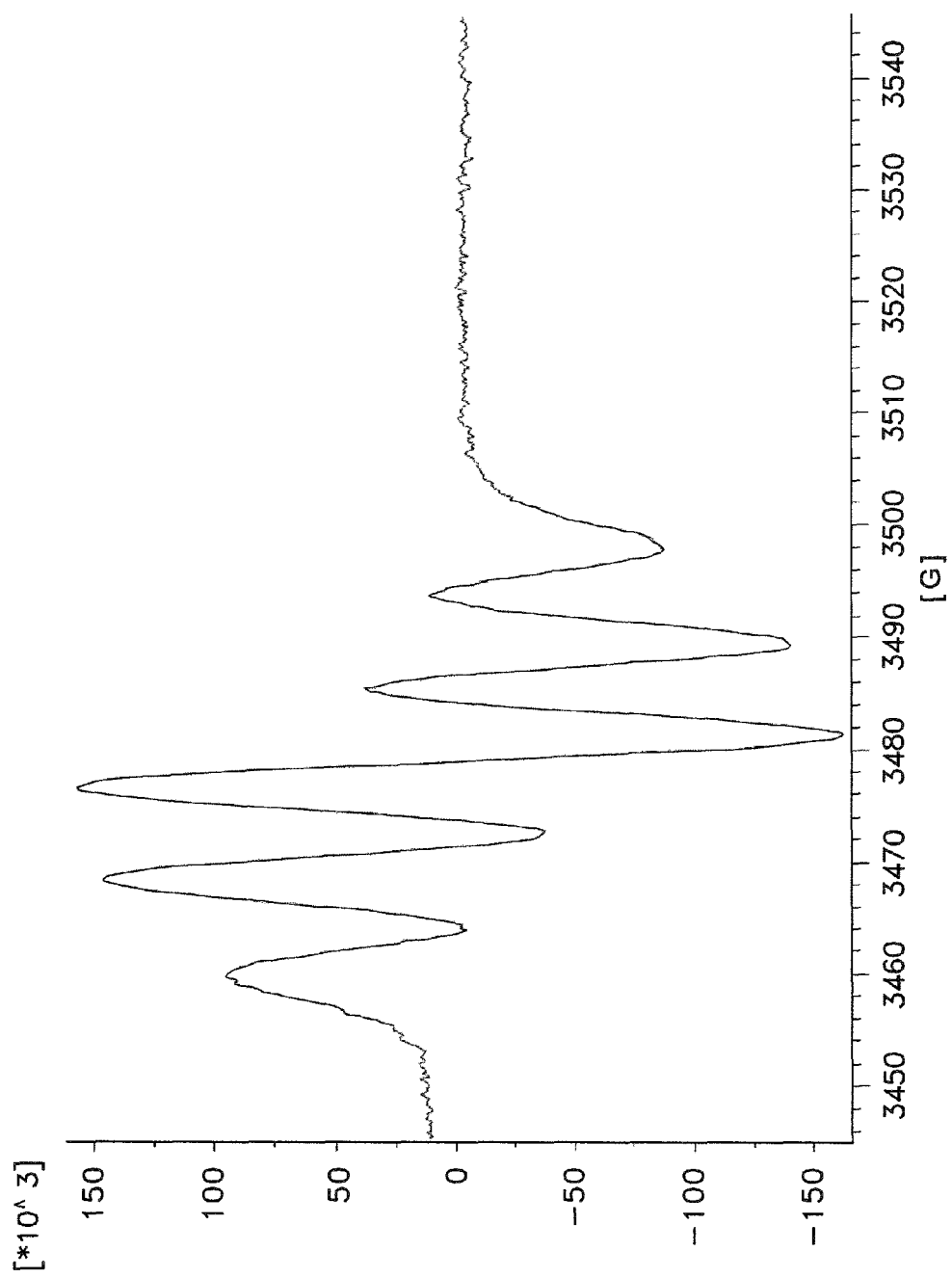
FIG. 2B is an electron paramagnetic resonance (EPR) signal plot for 2,2-diphenyl-1-picrylhydrazyl (DPPH) scavenging of product P1.
Figure 2C:
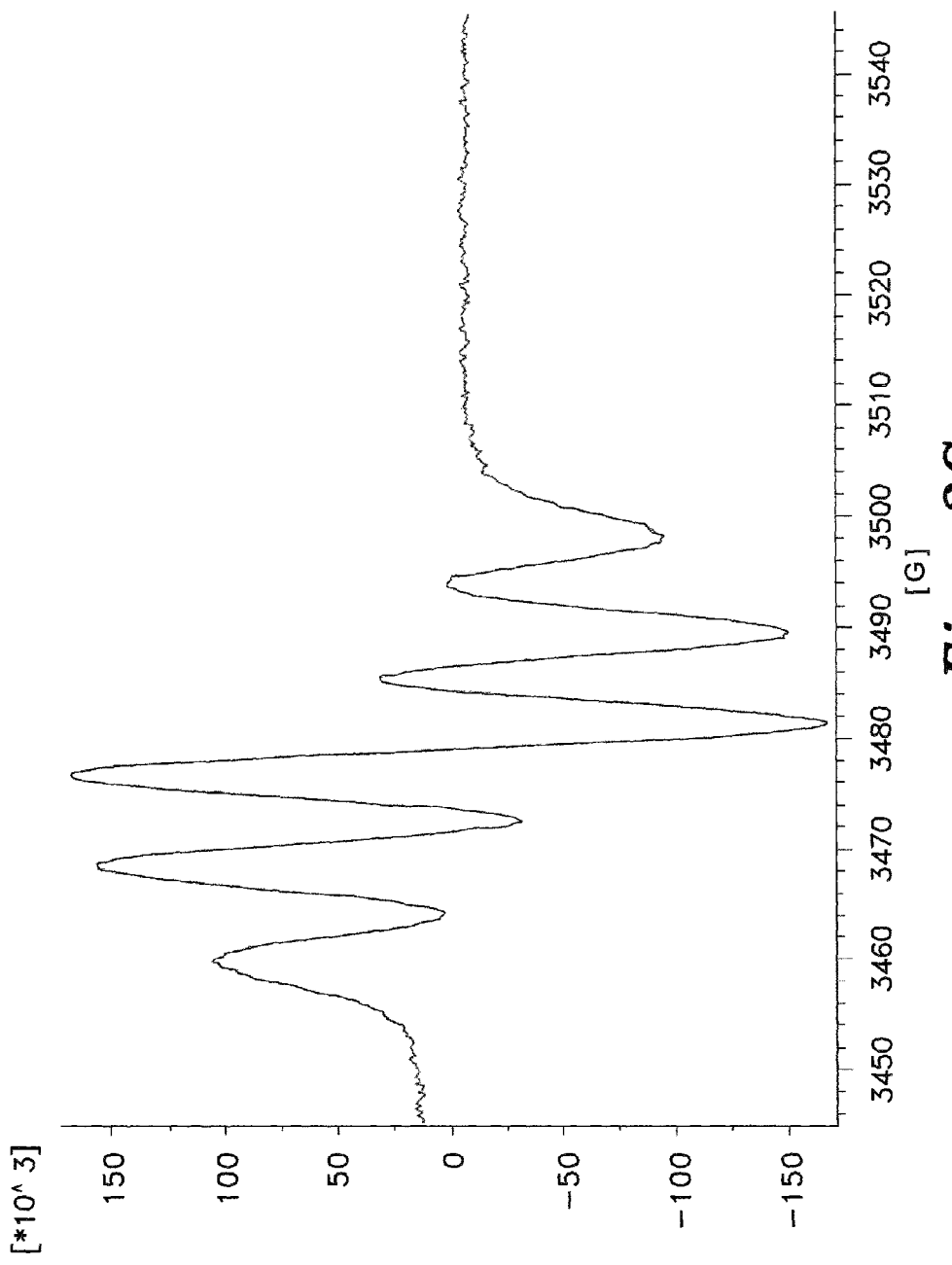
FIG. 2C is an electron paramagnetic resonance (EPR) signal plot for 2,2-diphenyl-1-picrylhydrazyl (DPPH) scavenging of product P2.
Figure 2D:
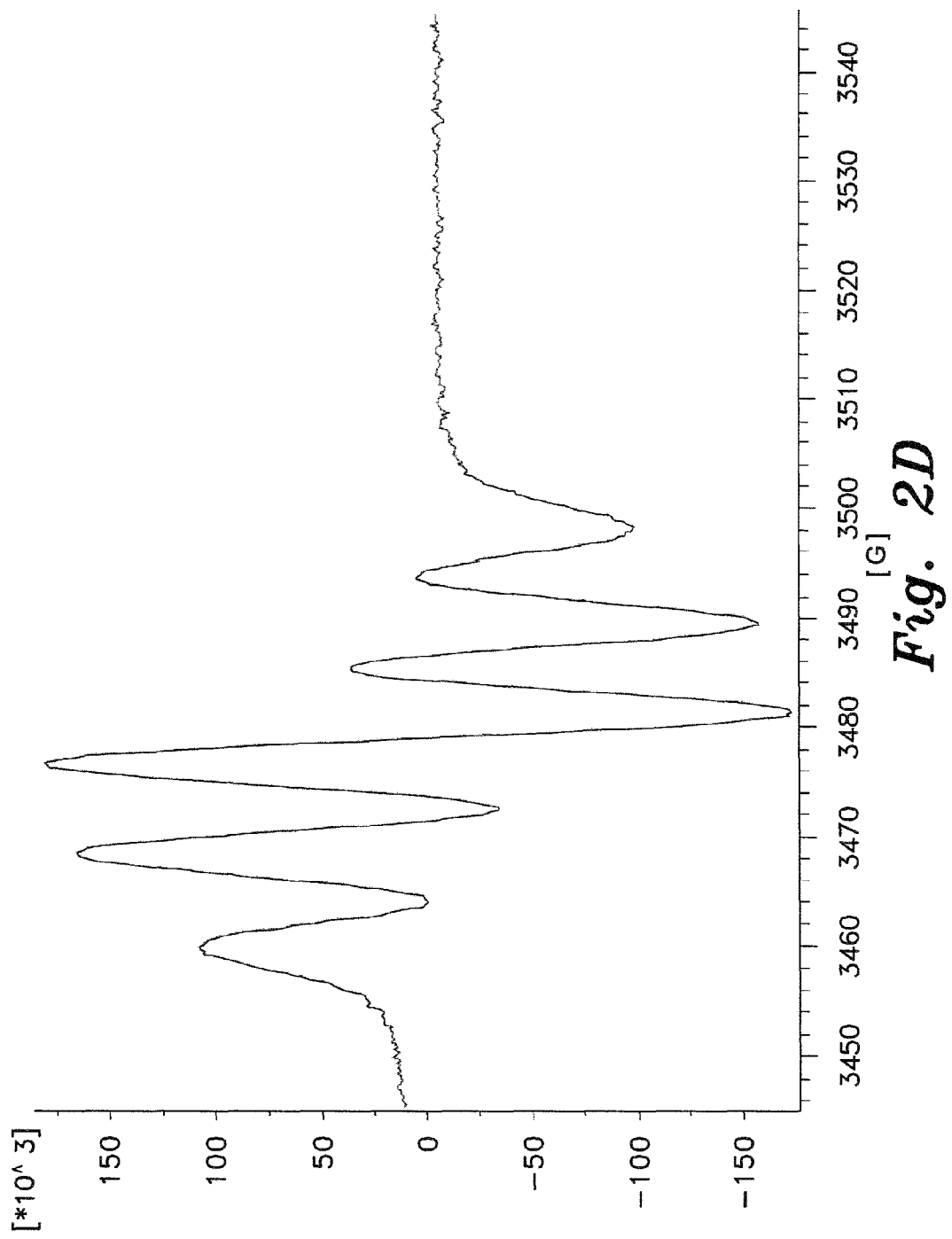
FIG. 2D is an electron paramagnetic resonance (EPR) signal plot for 2,2-diphenyl-1-picrylhydrazyl (DPPH) scavenging of product P3.
Figure 2E:
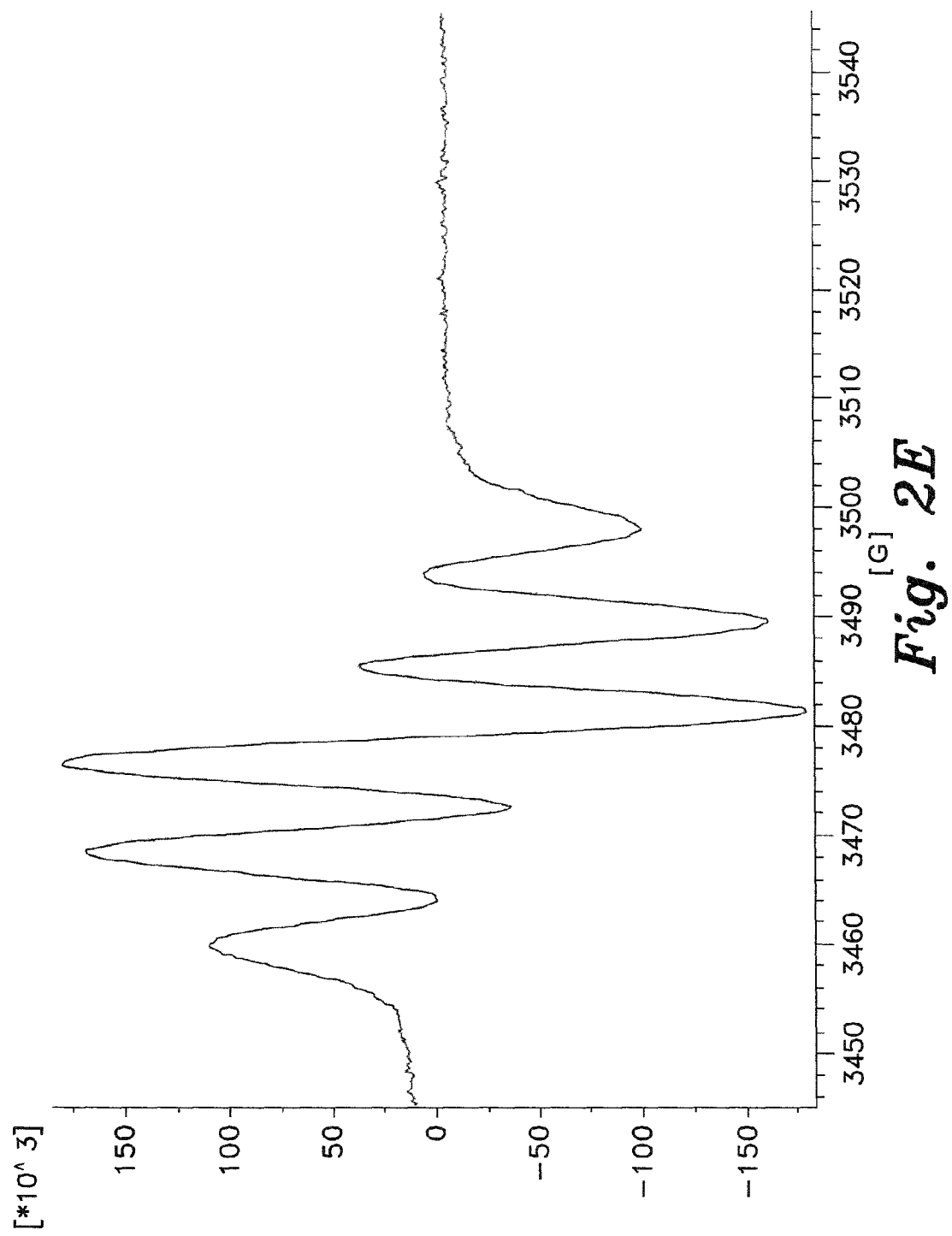
FIG. 2E is an electron paramagnetic resonance (EPR) signal plot for 2,2-diphenyl-1-picrylhydrazyl (DPPH) scavenging of a sample of unfermented camel milk supplemented with carrageenan (product P4).
Figure 2F:
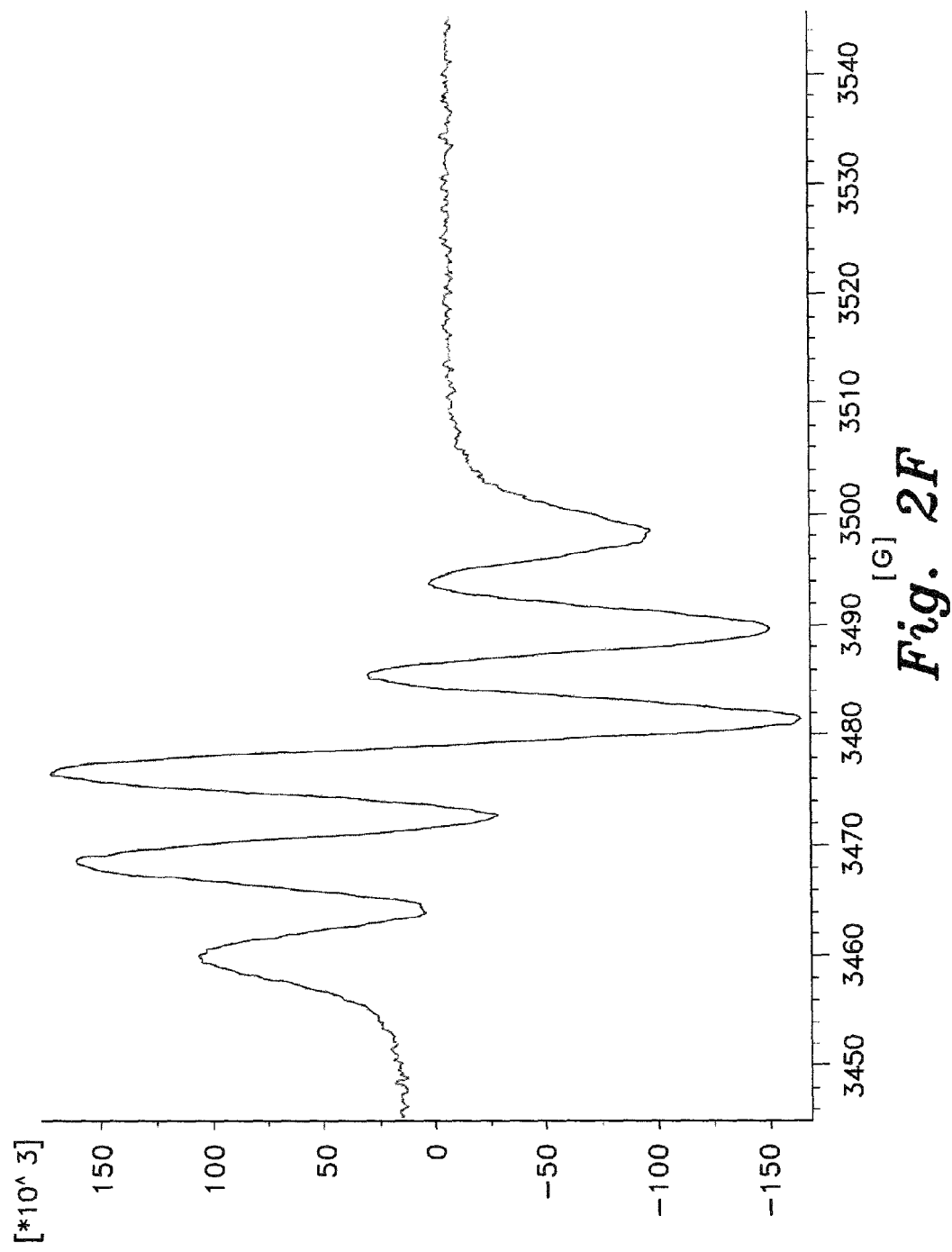
FIG. 2F is an electron paramagnetic resonance (EPR) signal plot for 2,2-diphenyl-1-picrylhydrazyl (DPPH) scavenging of a sample of unfermented camel milk without carrageenan (product P5).

The DPPH method determines the donation of hydrogen atoms or electrons to free radicals, resulting in more stable compounds. The electron paramagnetic resonance (EPR) spectra differences between fermented and un-fermented camel milk products are shown in FIGS. 2A-2F. FIG. 2A shows a "blank" plot for a control sample, and FIGS. 2B, 2C, 2D, 2E and 2F show plots for products P1, P2, P3, P4 and P5, respectively. As shown, the higher the DPPH radical scavenged by antioxidant, the lower EPR spectra intensity obtained. DPPH radical scavenging of fermented and unfermented camel milk followed an order of P3<P5~P4<P2<P1, and the values ranged from 0.03±0.0 to 0.08±0.0 μmol trolox equivalents per mg of protein (shown above in Table 2). The antioxidant capacity of protein hydrolysate was found to depend on the type of protease enzymes from lactic acid bacteria (LAB) involved in the hydrolysis of specific peptide bonds in milk protein structure, but not directly dependent on fermentation time. Bioactive peptides consisted of specific amino acids, including proline, lysine, methionine, glutamine, tyrosine, lysine, valine and cysteine, which were found to possess strong antioxidant activity.

The fermented camel milk products (P1 and P2) were found to exhibit higher DPPH radical scavenging activity than unfermented camel milk (P4 and P5). This is attributed to the addition of certain LAB strains to camel milk, which resulted in a higher content of specific amino acids that possess stronger antioxidant activity. Moreover, product P1 exhibited the strongest antioxidant capacity due to the presence of proline, lysine, methionine, glutamine and valine at higher percentages compared to other fermented and un-fermented products (as shown in Table 1).

The P3 product possessed the lowest DPPH radical scavenging activity, compared to the other fermented products, due to the high proteolytic activity of L. bulgaricus, which resulted in further degradation of antioxidant peptides. However, significant (p<0.05) differences in DPPH radical scavenging activity was noticed between product P1 and the other fermented and un-fermented products. These results are in agreement with studies performed on bovine milk, whereas samples containing L. acidophilus exhibited high antioxidant activity, while samples containing only yogurt culture (S. thermophilus and L. bulgaricus) exhibited the lowest activity.

The hydroxyl radical scavenging capacity was determined by preparing samples of products P1, P2, P3, P4 and P5 (200 μL) in 75 mM phosphate buffer (pH 7.2), which were mixed with 200 μL of $H_2O_2$ (10 mM), 400 μL of DMPO (17.6 mM) and 200 μL of $FeSO_4$ (10 mM). After 3 minutes, the samples were injected into the sample cavity of the EPR spectrometer and their spectra were recorded. Histidine, dissolved in 75 mM phosphate buffer (pH 7.2), was used to prepare the standard curve (0.1-2.0 mg/mL). Hydroxyl radical scavenging was generated from hydrogen peroxide ($H_2O_2$) via the Fe (II)-catalyzed Fenton reaction and spin-trapped with DMPO. Hydroxyl radical scavenging capacities were calculated as: Hydroxyl radical scavenging capacity (%)={ (EPR signal intensity for the control−EPR signal intensity for the sample)/EPR signal intensity for the control}×100. The hydroxyl radical scavenging activity of the samples, shown in Table 3 above, are expressed as micromoles of histidine equivalents per gram of sample.

Figure 3A:
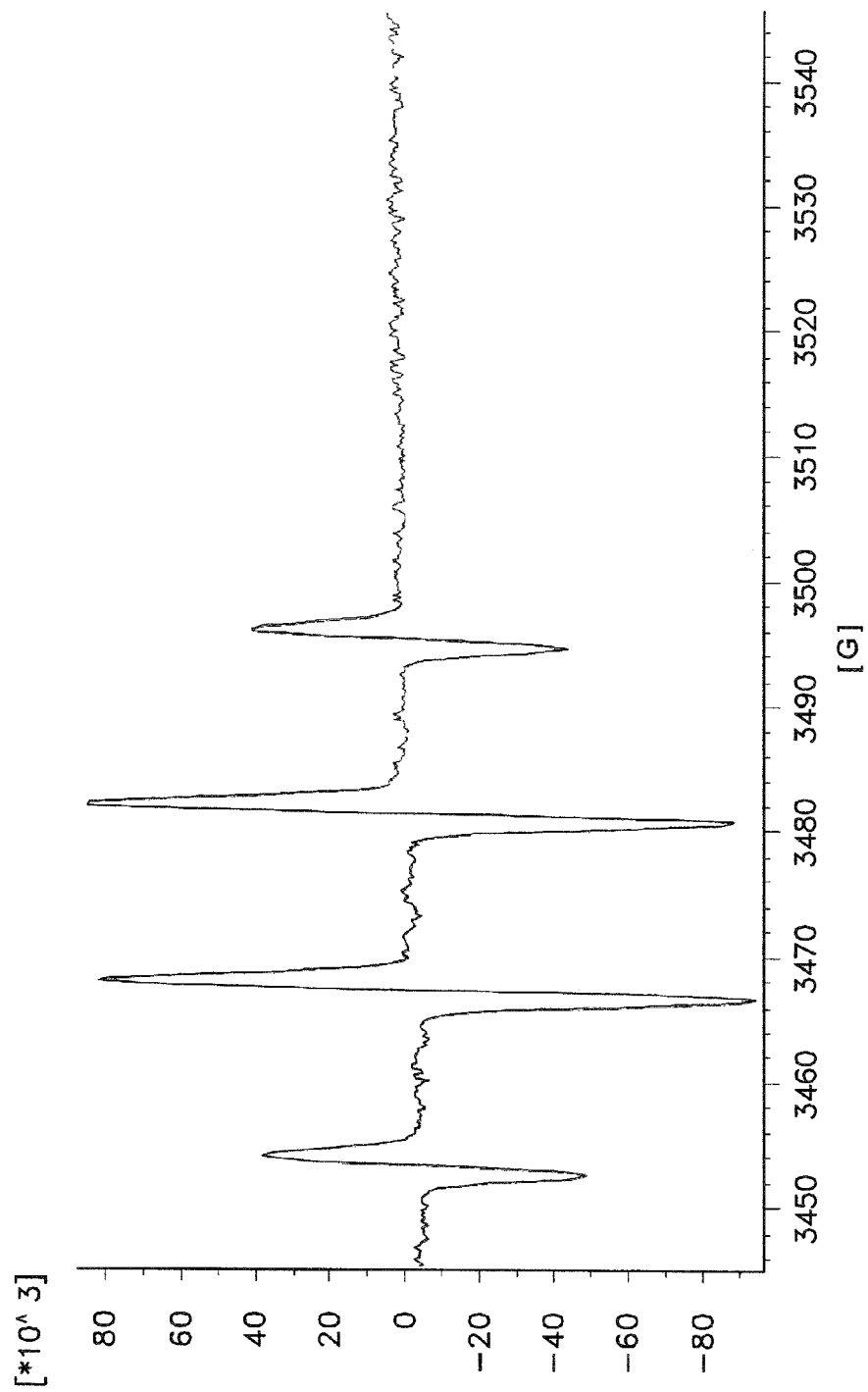
FIG. 3A is an electron paramagnetic resonance (EPR) signal (1:2:2:1) plot for DMPO-OH adduct of a control sample.
Figure 3B:
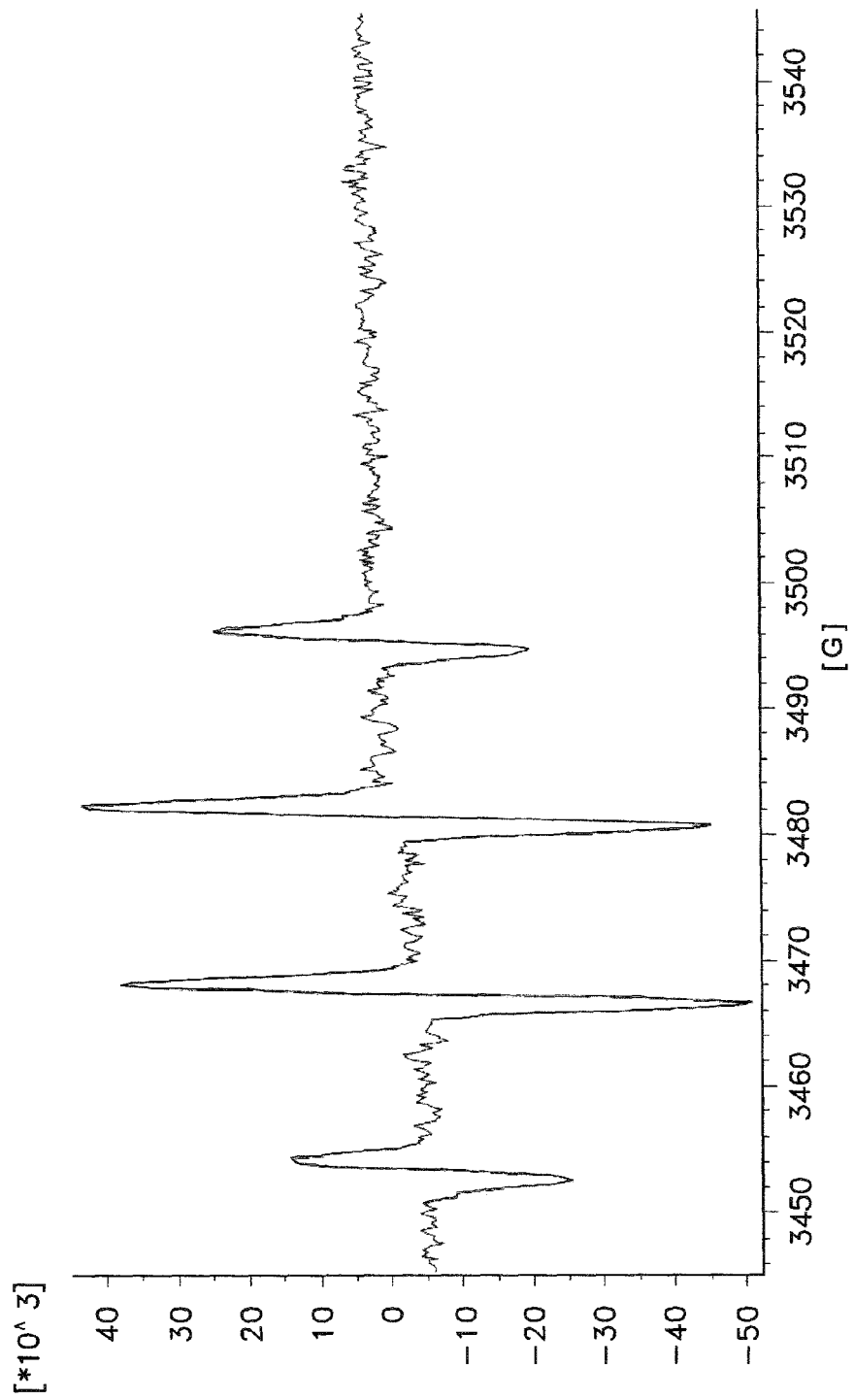
FIG. 3B is an electron paramagnetic resonance (EPR) signal (1:2:2:1) plot for DMPO-OH adduct of product P1.
Figure 3C:
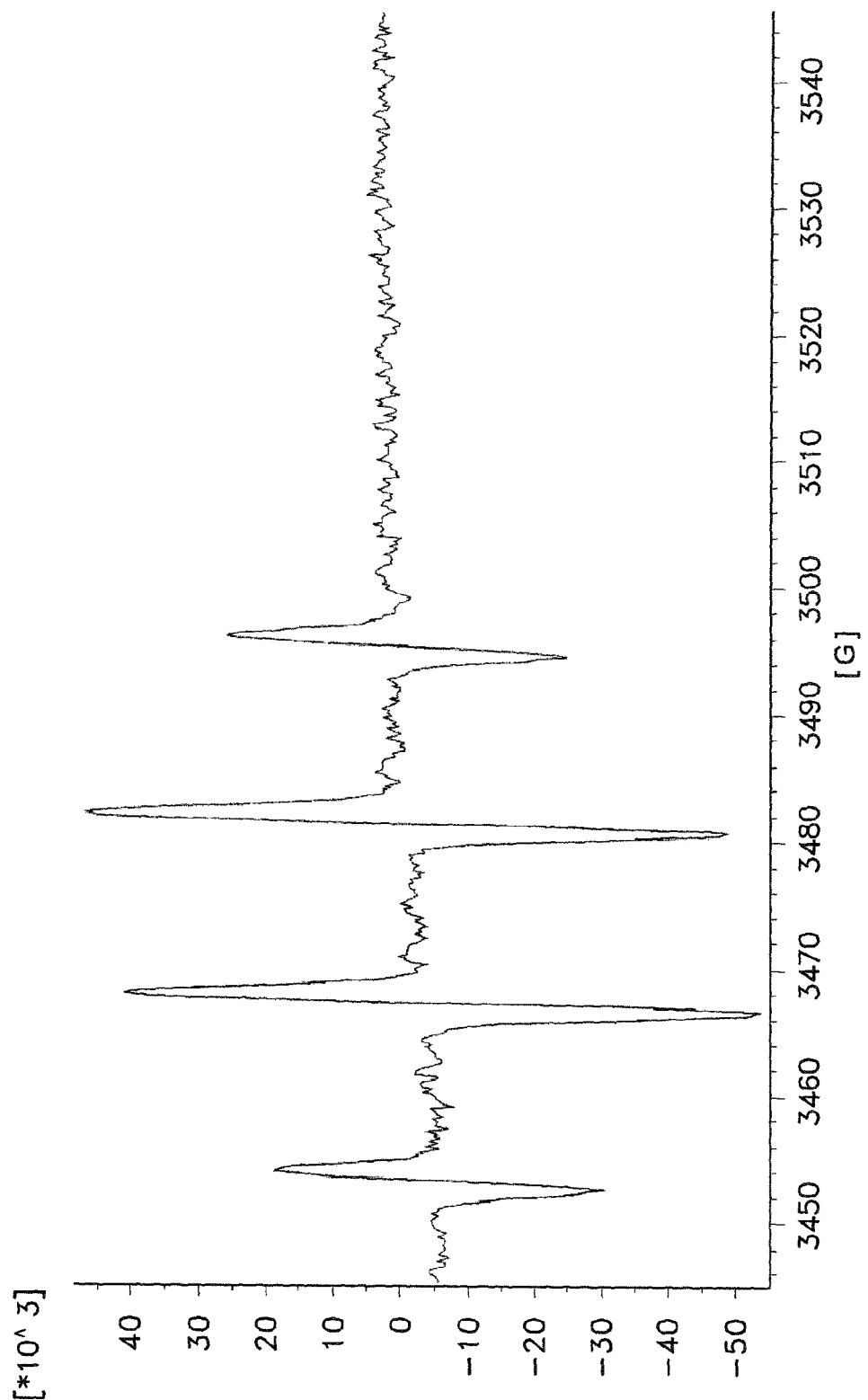
FIG. 3C is an electron paramagnetic resonance (EPR) signal (1:2:2:1) plot for DMPO-OH adduct of product P2.
Figure 3D:
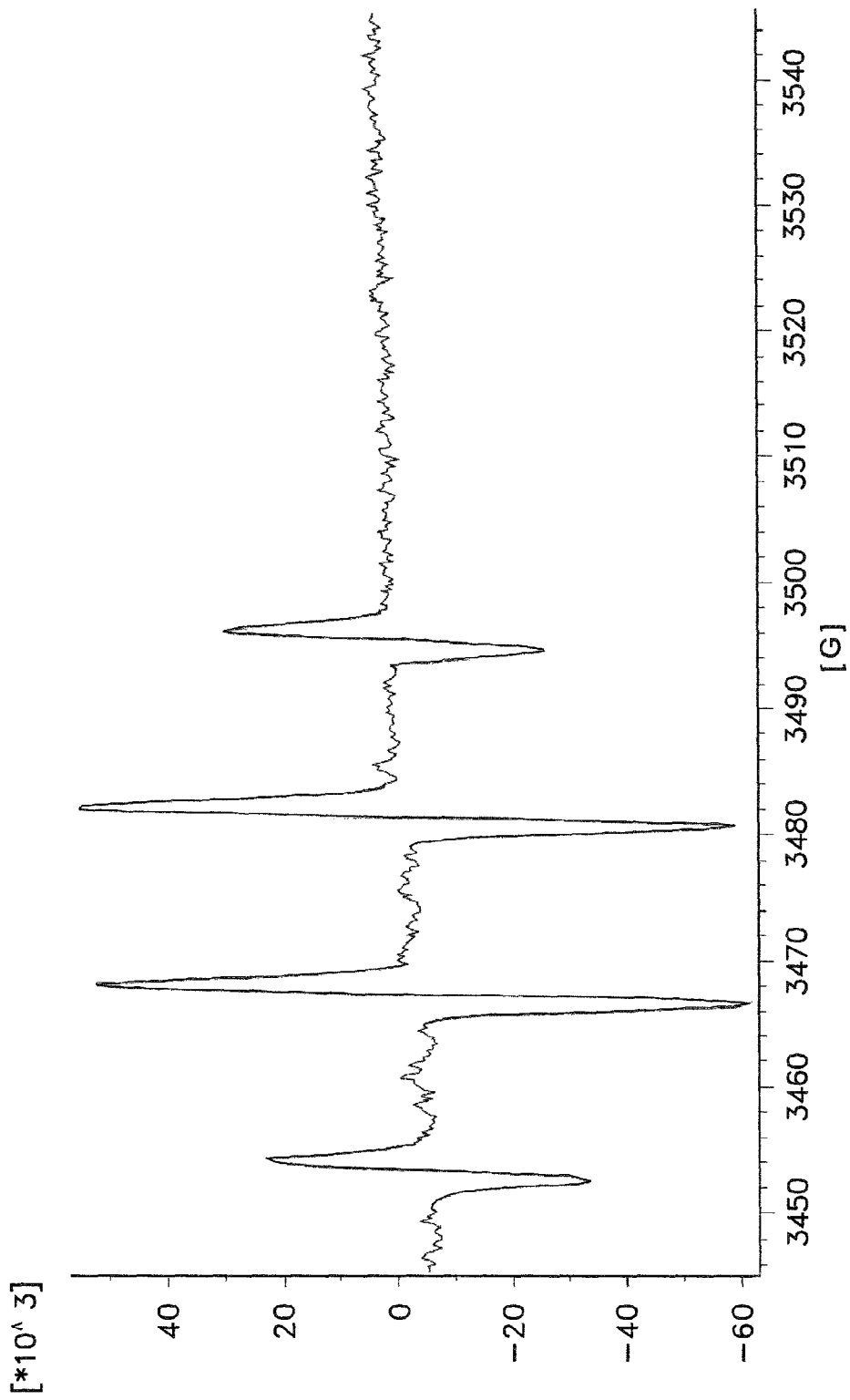
FIG. 3D is an electron paramagnetic resonance (EPR) signal (1:2:2:1) plot for DMPO-OH adduct of product P3.
Figure 3E:
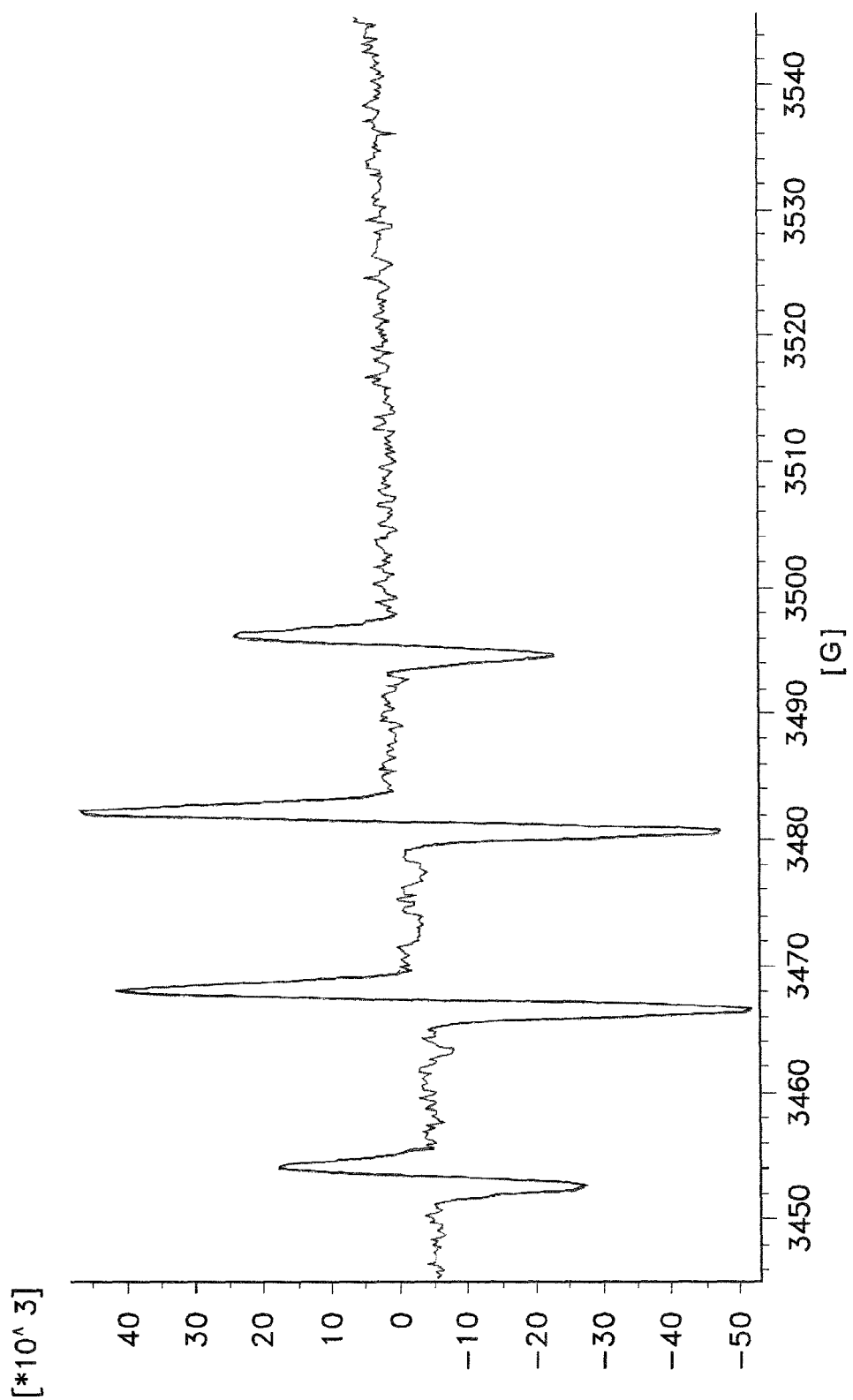
FIG. 3E is an electron paramagnetic resonance (EPR) signal (1:2:2:1) plot for DMPO-OH adduct of product P4.

The differences of the EPR signal detected as 1:2:2:1 of the DMPO-OH adduct of control, unfermented and fermented camel milk products are shown in FIGS. 3A-3F. FIG. 3A shows a plot for a control sample, and FIGS. 3B, 3C, 3D, 3E and 3F respectively show plots for products P1, P2, P3, P4 and P5. The relative amount of DMPO-OH adduct is represented as the height of the third peak of the spectrum. The lower the DMPO-OH adduct intensity, the higher the hydroxyl radical scavenging obtained. The hydroxyl radical scavenging activity of unfermented and fermented camel milk products are presented in Table 3 in terms of percentage and μmol of histidine equivalents per mg of protein. The lowest hydroxyl radical scavenging activity (25%) was found for product P3, while product P1 showed the highest activity (40%), as indicated in Table 3. A significant (p<0.05) difference was seen between hydroxyl radical scavenging activity of fermented and unfermented products, which increased in an order of P3<P5<P2~P4<P1.

Table 4 below shows antimicrobial activity of water soluble extracts (WSEs) containing bioactive peptides isolated from products P1, P2, P3 and P4 against some common pathogens. As with the results of Tables 1-3, the results are shown for products stored for one day at 4° C. In Table 4, +++ represents an extra-large inhibition zone (ca 20-25 mm); ++ represents a very large inhibition zone (ca 14-19 mm); + represents a large inhibition zone (ca 11-13 mm); ± represents a medium inhibition zone (ca 8-10 mm); and − represents no inhibition zone.

TABLE 4

Antimicrobial activity of water soluble extracts (WSEs) containing bioactive peptides isolated from products P1, P2, P3 and P4

| Pathogens | Diameter of inhibition zones (mm) | | | |
|---|---|---|---|---|
| | P1 | P2 | P3 | P4 |
| B. cereus | ± | ++ | ± | − |
| E. coli | +++ | ++ | − | − |
| Salmonella | +++ | ++ | − | − |
| Staphylococcus | ++ | + | − | − |

In Table 4 above, the antimicrobial effect of fermented camel milk products (Pt, P2 and P3) were examined and compared against those of unfermented camel milk (P4) with an inhibition zone diameter (mm) of WSEs (50 µL) from unfermented and fermented camel milk (P1, P2, P3 and P4) against pathogens being measured using a diffusion test in Müller Hinton agar medium after one day of storage. Four overnight pathogenic cultures (*Bacillus cereus, Escherichia coli, Salmonella typhimurium* and *Staphylococcus aureus*) were used as indicator bacteria.

Product P1 exhibited good inhibition zones against pathogens after one day of storage, the major effect being against *Salmonella typhimurium* and *E. coli*. The inhibition zones diameters were extra-large and ranged between 20-25 mm. On the other hand, a smaller inhibition zone was seen against *B. cereus*, and the inhibition zone diameter was medium and ranged between 8-10 mm. Product P2 exhibited very large inhibition zones against *B. cereus, E. coli* and *Salmonella* after one day of storage. However, the inhibition zone diameters ranged between 14-19 mm. *Staphylococcus* was less sensitive to product P2, and the inhibition diameter was between 11-13 mm. Unfermented camel milk product supplemented with carrageenan (product P4) showed no antimicrobial effect against any of the tested pathogens. Product P3 exhibited low antimicrobial activity against *B. cereus* only, and none against the other pathogens. This is because commercial yogurt culture has high proteolytic activity and could form or hydrolyze antimicrobial peptides very quickly.

As noted above, in order to determine the nutritional and antimicrobial benefits of the camel milk products, WSEs were prepared, specifically by centrifugation at 12,000 g for 10 minutes at a temperature of 4° C., followed by filtering through a millipore syringe filter (45 µm). The WSEs of the unfermented camel milk control sample were prepared by adding 7% lactic acid to the milk to reach a pH of 4.4, followed by filtration. The resultant WSEs of all samples were collected in 1.5 mL Eppendorf tubes and stored at −20° C. until use. As will be described in detail below, additional factors, including total probiotic bacteria, and the sensory and textual attributes of the fermented camel milk products were determined for up to 15 days and 21 days of storage, respectively, to make sure the fermented products were stable during this period.

The total bacterial counts of products P1, P2 and P3 were taken using the pour plate method. Serial dilutions of products P1, P2 and P3 were achieved in sterile 0.15% (w/v) peptone water. An aliquot of 1 mL of dilution was used for enumeration in MRS agar medium and incubated at 37° C. for 72 hours under anaerobic conditions. Colony forming units (CFU) per mL of each sample were counted. The average of total bacterial counts of products P1, P2 and P3 were determined at intervals after 1 day, 5 days, 10 days, and 15 days of storage, and were represented as Log CFU/mL.

The average of bacterial counts after one day of storage were $9.5 \times 10^7$, $2 \times 10^8$ and $1.7 \times 10^8$ CFU/mL in products P1, P2 and P3, respectively. The total counts of products P1, P2 and P3 were then increased after 5 days of storage and recorded as $3.5 \times 10^8$, $5.8 \times 10^8$ and $4.3 \times 10^8$ CFU/mL, respectively, as shown in FIG. 1. The total counts at the end of storage (15 days) reached their maxima, and were recorded as $5 \times 10^8$ and $8.15 \times 10^8$ CFU/mL for products P1 and P2, respectively. These numbers are above the minimum level ($10^7$ CFU/mL) of probiotic proposed by EU guidelines to provide probiotic health claims during a product's shelf life.

With regard to sensory properties of the products, the fermented camel milk products were evaluated by 12 highly-trained, descriptive panelists. Selected panelists completed over 120 minutes of general training in descriptive sensory attributes, which included exposure to dairy products. The scores of sensory attributes, including appearance, odor, taste, flavor, mouth feel, texture and overall acceptability, were determined using 7 hedonic scales after one day, seven days, 14 days, and 21 days of storage.

Among the fermented camel milk products, product P3 had the lowest score for all attributes except appearance. The results showed no significant differences (p>0.05) among all fermented milk products tested in the average score of appearance and overall acceptability (see Table 5 below). On the other hand, taste, flavor, mouth feel and texture scores after one day of storage were higher in fermented milk product P2 than fermented milk product P1, but not particularly significant (p>0.05). In contrast, these attributes showed significant differences (p>0.05) between products P2 and P3, except for scores of texture. The taste score was significant (p>0.05) between products P2 and P3, whereas no significant differences (p>0.05) were found in the mean score of flavor, mouth feel and texture between products P1 and P2.

The sensory attribute scores of fermented camel milk products after seven days of storage, including appearance, odor, taste, flavor, mouth feel, texture and overall acceptability, showed no significant differences (p>0.05) between products P1 and P2 (see Table 6 below). However, significant differences (p>0.05) were found between products P3 and products P1 and P2 in relation to taste, flavor and overall acceptability attributes after seven days of storage. In general, no significant differences (p>0.05) were found among all sensory attribute scores of the fermented products (P1, P2 and P3) after 14 days of storage except for the overall acceptance score between products P2 and P3 (see Table 7 below). On the other hand, taste, flavor, mouth feel and overall acceptability scores of product P3 after 21 days of storage were significantly different (p>0.05) from those of products P1 and P2, as shown in Table 8 below. The overall acceptability scores of the fermented camel milk products were ordered as follows: P2>P1>P3. Furthermore, product P2 scored highest acceptability, while product P3 scored the lowest among fermented camel milk products. Product P3 developed high acidity, especially in the last two weeks of the experiment, due to the presence of *L. bulgaricus* strain in P3. Therefore, the taste and overall acceptance of this product was lower than the other two products.

TABLE 5

Sensory Scoring of Products P1, P2 and P3 after 1 Day of Storage

|  | P1 | P2 | P3 |
|---|---|---|---|
| Appearance | $6.000^a \pm 0.816$ | $5.938^a \pm 1.063$ | $6.188^a \pm 0.750$ |
| Aroma | $5.250^b \pm 1.000$ | $5.563^{ab} \pm 0.727$ | $6.063^a \pm 0.929$ |
| Taste | $5.000^{ab} \pm 1.317$ | $5.688^a \pm 1.195$ | $4.375^b \pm 0.806$ |
| Flavor | $5.000^a \pm 1.366$ | $5.188^a \pm 1.047$ | $4.250^b \pm 0.856$ |
| Mouth texture | $5.125^{ab} \pm 0.719$ | $5.313^a \pm 0.873$ | $4.688^{bc} \pm 0.793$ |
| Texture | $5.063^a \pm 0.929$ | $5.500^a \pm 1.095$ | $4.750^{ab} \pm 1.065$ |
| Acceptance | $4.875^a \pm 0.885$ | $5.063^a \pm 0.998$ | $4.438^a \pm 0.814$ |

TABLE 6

Sensory Scoring of Products P1, P2 and P3 after 7 Days of Storage

|  | P1 | P2 | P3 |
|---|---|---|---|
| Appearance | $5.563^a \pm 0.964$ | $5.375^{ab} \pm 1.147$ | $5.813^a \pm 0.834$ |
| Aroma | $5.125^a \pm 1.147$ | $5.250^a \pm 0.856$ | $4.813^a \pm 1.759$ |
| Taste | $5.063^a \pm 1.124$ | $5.188^a \pm 0.911$ | $3.625^b \pm 1.204$ |
| Flavor | $5.063^a \pm 1.063$ | $5.125^a \pm 0.885$ | $4.000^b \pm 1.461$ |
| Mouth texture | $5.250^a \pm 1.183$ | $5.438^a \pm 0.892$ | $3.813^b \pm 1.223$ |
| Texture | $5.438^a \pm 0.964$ | $5.438^a \pm 1.094$ | $4.688^{ab} \pm 1.195$ |
| Acceptance | $5.063^a \pm 1.063$ | $5.375^a \pm 0.619$ | $4.125^b \pm 1.204$ |

TABLE 7

Sensory Scoring of Products P1, P2 and P3 after 14 Days of Storage

|  | P1 | P2 | P3 |
|---|---|---|---|
| Appearance | $5.200^a \pm 0.789$ | $5.300^a \pm 0.483$ | $5.400^a \pm 0.516$ |
| Aroma | $4.700^a \pm 0.823$ | $4.900^a \pm 0.738$ | $4.800^a \pm 1.033$ |
| Taste | $3.900^b \pm 0.568$ | $5.200^a \pm 0.789$ | $4.800^a \pm 1.619$ |
| Flavor | $4.300^a \pm 0.675$ | $5.100^a \pm 0.876$ | $4.900^a \pm 1.595$ |
| Mouth texture | $4.300^a \pm 0.949$ | $5.000^a \pm 0.471$ | $4.700^a \pm 1.494$ |
| Texture | $4.600^a \pm 0.699$ | $5.100^a \pm 0.316$ | $5.200^a \pm 1.229$ |
| Acceptance | $4.100^{ab} \pm 0.568$ | $5.300^a \pm 0.675$ | $4.800^b \pm 1.476$ |

TABLE 8

Sensory Scoring of Products P1, P2 and P3 after 21 Days of Storage

|  | P1 | P2 | P3 |
|---|---|---|---|
| Appearance | $5.467^a \pm 0.640$ | $5.600^a \pm 0.632$ | $5.800^a \pm 0.775$ |
| Aroma | $5.200^a \pm 0.561$ | $5.333^a \pm 0.816$ | $5.133^a \pm 1.060$ |
| Taste | $5.133^a \pm 0.743$ | $5.267^a \pm 0.799$ | $4.133^b \pm 1.642$ |
| Flavor | $5.267^a \pm 0.704$ | $5.400^a \pm 0.828$ | $4.333^b \pm 1.496$ |
| Mouth texture | $5.067^{ab} \pm 0.884$ | $5.533^a \pm 0.834$ | $4.600^b \pm 1.352$ |
| Texture | $5.200^a \pm 0.941$ | $5.333^a \pm 0.900$ | $5.067^a \pm 0.594$ |
| Acceptance | $5.267^a \pm 0.884$ | $5.467^a \pm 0.834$ | $4.267^b \pm 1.335$ |

The highest viscosity after one day of storage was recorded for product P2, whereas the lowest value was found for product P3. The viscosity value of all fermented camel milk products (P1, P2 and P3) after one day of storage were significantly different (p>0.05) and were as follows: 25.375, 36.25 and 8.375 CP, respectively, as shown below in Table 9.

The apparent viscosity of all fermented camel milk products gradually decreased after 7 days, 14 days and 21 days of storage at 4° C., but remained significantly different (p>0.05), as shown in Tables 10, 11 and 12, below. The apparent viscosity value of product P1 decreased from 25.375 CP to 11.495 CP after 21 days of storage. The viscosity of product P2 decreased from 36.25 CP to 26.1 CP after 21 days of storage. Moreover, the viscosity values of product P3 were slightly decreased from 8.375 CP to 4.85 CP during 21 days of storage.

TABLE 9

Textural Attributes of Products P1, P2 and P3 after 1 Day of Storage

| Attributes | P1 | P2 | P3 |
|---|---|---|---|
| Viscosity | $25.375^b \pm 1.225$ | $36.253^a \pm 1.25$ | $8.375^c \pm 1.225$ |
| Hard 1 | $3.667^a \pm 0.577$ | $4.333^a \pm 0.577$ | $4.000^a \pm 1.000$ |
| Hard 2 | $3.667^a \pm 0.577$ | $4.333^a \pm 0.577$ | $3.000^a \pm 1.000$ |
| Cohesiveness | $0.830^a \pm 0.075$ | $0.883^a \pm 0.032$ | $1.207^a \pm 0.601$ |
| Springiness | $7.600^a \pm 1.114$ | $9.433^a \pm 1.332$ | $7.767^a \pm 1.986$ |

TABLE 10

Textural Attributes of Products P1, P2 and P3 after 7 Days of Storage

| Attributes | P1 | P2 | P3 |
|---|---|---|---|
| Viscosity | $21.05^b \pm 2.250$ | $35.25^a \pm 1.950$ | $7.44^c \pm 2.31$ |
| Hard 1 | $4.333^a \pm 0.577$ | $3.333^a \pm 0.577$ | $4.333^a \pm 1.528$ |
| Hard 2 | $4.000^a \pm 0.000$ | $3.667^a \pm 1.155$ | $4.333^a \pm 1.528$ |
| Cohesiveness | $0.857^a \pm 0.012$ | $0.773^a \pm 0.006$ | $0.847^a \pm 0.115$ |
| Springiness | $7.033^a \pm 0.651$ | $8.133^a \pm 0.850$ | $8.600^a \pm 0.700$ |

TABLE 11

Textural Attributes of Products P1, P2 and P3 after 14 Days of Storage

| Attributes | P1 | P2 | P3 |
|---|---|---|---|
| Viscosity | $11.05^c \pm 4.25$ | $30.2^b \pm 3.6$ | $6.55^c \pm 1.25$ |
| Hard 1 | $4.000^a \pm 0.000$ | $4.667^a \pm 0.577$ | $4.667^a \pm 1.528$ |
| Hard 2 | $3.333^b \pm 0.577$ | $5.333^a \pm 0.577$ | $4.667^{ab} \pm 1.528$ |
| Cohesiveness | $0.843^a \pm 0.119$ | $0.930^a \pm 0.035$ | $0.727^a \pm 0.352$ |
| Springiness | $7.933^a \pm 1.767$ | $8.167^a \pm 0.814$ | $6.800^a \pm 2.651$ |

TABLE 12

Textural Attributes of Products P1, P2 and P3 after 21 Days of Storage

| Attributes | P1 | P2 | P3 |
|---|---|---|---|
| Viscosity | $11.495^a \pm 1.805$ | $26.1^b \pm 1.4$ | $4.85^c \pm 1.1$ |
| Hard 1 | $4.333^a \pm 1.155$ | $3.667^{ab} \pm 0.577$ | $2.667^b \pm 0.577$ |
| Hard 2 | $2.667^a \pm 2.517$ | $3.667^a \pm 0.577$ | $2.667^a \pm 0.577$ |
| Cohesiveness | $0.553^a \pm 0.486$ | $1.000^a \pm 0.135$ | $0.692^a \pm 0.196$ |
| Springiness | $8.267^a \pm 1.626$ | $8.867^a \pm 0.306$ | $8.167^a \pm 2.554$ |

In general, few significant differences (p>0.05) were found between all fermented camel milk products (P1, P2 and P3) in relation to hardness, cohesiveness and springiness during 21 days of storage, as shown in Table 12 above.

It is to be understood that the present invention is not limited to the embodiments described above, but encompasses any and all embodiments within the scope of the following claims.

We claim:

1. A method of making a fermented dairy product from camel milk, comprising the steps of:
adding an effective amount of a stabilizer to camel milk for reducing whey separation, wherein the stabilizer consists of κ-carrageenan, further wherein the step of adding an effective amount of κ-carrageenan to the camel milk consists of adding the κ-carrageenan to the camel milk to form a mixture having a κ-carrageenan concentration of 0.02 wt %;

fermenting the camel milk with a probiotic bacterial culture consisting of *Streptococcus thermophilus* and *Lactobacillus bulgaricus* until a pH of 4.4 is attained, wherein the step of fermenting the camel milk with the probiotic bacterial culture comprises fermenting the camel milk at a temperature of 40° C. for 10 hours;

storing the fermented camel milk at a temperature of 10° C. for 14 hours; and further storing the fermented camel milk in a refrigerator at a temperature of 4° C. for between 1 and 15 days.

2. The method of making a fermented dairy product as recited in claim 1, wherein the camel milk comprises milk from a *Camelus dromedarius*.

3. The method of making a fermented dairy product as recited in claim 2, further comprising the steps of:

heat treating the camel milk at a temperature of 85° C. for 30 minutes for preventing protein precipitation; and cooling the camel milk to a temperature of 60° C. prior to the step of adding the κ-carrageenan to the camel milk.

* * * * *